United States Patent
Romani et al.

(10) Patent No.: US 6,506,863 B2
(45) Date of Patent: Jan. 14, 2003

(54) ESTERS OF 3-(2-FURYL)-2-PROPENOIC ACID WITH DIOLS

(75) Inventors: Francesco Romani, Sarzana (IT); Vittorio Braga, deceased, late of Ferrara (IT), by Silva Pellizzari, legal representative

(73) Assignee: Basell Poliolefine Italia S.p.A., Milan (IT)

(*) Notice: Subject to any disclaimer, the term of this patent is extended or adjusted under 35 U.S.C. 154(b) by 0 days.

(21) Appl. No.: 10/017,343

(22) Filed: Dec. 14, 2001

(65) Prior Publication Data

US 2002/0137881 A1 Sep. 26, 2002

(30) Foreign Application Priority Data

Dec. 19, 2000 (IT) .......................... MI20A2748

(51) Int. Cl.⁷ .................... C08F 34/00; C08G 65/20; C07D 207/30
(52) U.S. Cl. .................. 526/270; 526/271; 528/403; 548/562
(58) Field of Search ................. 526/270, 271; 528/403; 548/562

(56) References Cited

U.S. PATENT DOCUMENTS 3,301,837 A * 1/1967 Bartorelli et al. ........... 526/270

OTHER PUBLICATIONS

O. Nuyken et al., Die Angewandte Makromolekulare Chemie, 199: 149–170 (1992).

* cited by examiner

Primary Examiner—James J. Seidleck
Assistant Examiner—Olga Asinovsky

(57) ABSTRACT

Esters of 3-(2-furyl)-2-propenoic acid with diols having the general formula $A_2X$, in which A is a 3-(2-furyl)-2-propenoate group and X is a $C_1$–$C_6$ alkylene group.

The said esters are used as crosslinking agents in processes for crosslinking polymers.

11 Claims, No Drawings

ESTERS OF 3-(2-FURYL)-2-PROPENOIC ACID WITH DIOLS

The present invention relates to organic furan compounds and to the process for synthesizing them. The invention also relates to a process for crosslinking polymers and to the polymers thus obtained.

The novel organic furan compounds are particularly suitable as chain-extending agents in the process for crosslinking or branching polymers.

Organic furan compounds containing at least two furyl rings are already known. Compounds that are well known are furfuraldazine and bis(furfurylidene)acetone, which are used as agents for crosslinking polymers.

The abovementioned furfuryl derivatives, currently used as crosslinking agents, have a number of drawbacks. One drawback is the dark brown coloration acquired by polymers when they are crosslinked with the known furfuryl derivatives. In addition, the known furfuryl derivatives are not easy to manipulate. The reason for this is that a certain number of the said furfuryl derivatives are hazardous to human health, since the said derivatives have mutagenic properties. In addition, they have the property of soiling materials with which they come into contact. At high temperature, materials containing the soiling furfuryl derivatives can release the soiling due to the effect of its volatility, even if they are not in direct contact with other materials.

The abovementioned furan compounds also comprise the category of polyol esters of 3-(2-furyl)-2-propenoic acid. Known compounds belonging to this category are diol esters containing fluorine atoms in the alkylene chain, which are described in "Die Angewandte Makromoleculare Chemie 199 (1992) 149–170". These diol esters are used for preparing partially fluorinated photopolymers.

Novel diol esters of 3-(2-furyl)-2-propenoic acid have now been found which do not have the abovementioned drawbacks when used as agents in the process for crosslinking or branching polymers.

In addition, the esters according to the present invention show high reactivity with polymers in radical form. Thus, they are capable of crosslinking the polymer even if they are used in very low amounts.

The present invention thus provides diol esters of 3-(2-furyl)-2-propenoic acid having the following general formula:

$$A_2X \qquad (I)$$

in which
A is

and X is a $C_1$–$C_6$ alkylene group. The alkylene group may contain one or more substituents (in place of one or more hydrogen atoms) chosen from linear or branched $C_1$–$C_{20}$ alkyl radicals, $C_3$–$C_{18}$ cycloalkyl radicals, $C_6$–$C_{18}$ aryl radicals, for instance a phenyl group, or $C_7$–$C_{20}$ arylalkyl radicals. The cycloalkyl and aryl radicals may also contain one or more substituents such as a $C_1$–$C_{20}$ alkyl group.

Preferably X is an alkylene group containing two, three or four carbon atoms.

The diol esters of the present invention are free of halogens.

Specific examples are the following esters:

methanediyl bis[3-(2-furyl)-2-propenoate];
phenylmethanediyl bis[3-(2-furyl)-2-propenoate];
1,2-ethanediyl bis[3-(2-furyl)-2-propenoate];

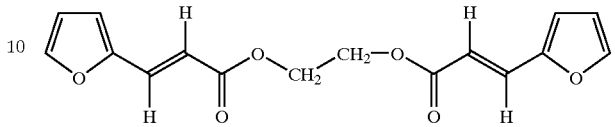

1,3-propanediyl bis[3-(2-furyl)-2-propenoate]:

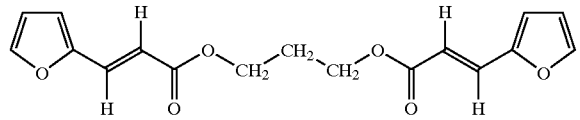

1,2-propanediyl bis[3-(2-furyl)-2-propenoate];
1,3-butanediyl bis[3-(2-furyl)-2-propenoate];
1,4-butanediyl bis[3-(2-furyl)-2-propenoate];
2,3-butanediyl bis[3-(2-furyl)-2-propenoate];
1,5-pentanediyl bis[3-(2-furyl)-2-propenoate];
1,6-hexanediyl bis[3-(2-furyl)-2-propenoate];
4-methyl-2,4-pentanediyl bis[3-(2-furyl)-2-propenoate].

The novel esters may be synthesized according to various processes. For example, they may be sythesized by known esterification reactions, by reacting the corresponding saturated aliphatic alcohols containing two hydroxyl groups (diols) with 3-(2-furyl)-2-propenoic acid or derivatives thereof, for instance acyl halides and anhydrides.

Both the said alcohols and the 3-(2-furyl)-2-propenoic acid are well-known compounds. Examples of diols are 1,2-ethanediol, 1,2-propanediol, 1,3-propanediol, 1,3-butanediol, 1,4-butanediol, 2,3-butanediol, 4-methyl-2,4-pentanediol and 1,5-pentanediol.

The methanediyl bis[3-(2-furyl)-2-propenoate] may be synthesized by reacting 3-(2-furyl)-2-propenoic acid or the corresponding anhydride with formaldehyde in the presence of an acid catalyst, such as p-toluenesulphonic acid. The methanediyl bis[3-(2-furyl)-2-propenoate] is then separated from the by-products, for example by chromatography.

The phenylmethanediyl bis[3-(2-furyl)-2-propenoate] may be synthesized by reacting 3-(2-furyl) -2-propenoic anhydride with toluene in the presence of $CrO_3$.

The present invention also provides a crosslinkable polymer composition which comprises a crosslinkable polymer, an ester of formula (I) and a free-radical initiator, and a process for crosslinking polymers in the presence of a free-radical initiator and an ester of formula (I). Any crosslinkable polymer, either homopolymers or copolymers, and blends thereof, may be used in the present invention. However, polyolefins are preferred.

Suitable examples are crystalline and partially crystalline polymers of α-olefins $CH_2=CHR$, in which R is a hydrogen radical or a $C_1$–$C_8$ alkyl radical. Polymers that are particularly preferred are ethylene polymers, for instance HDPE, LDPE and LLDPE, propylene polymers, especially isotactic or mainly isotactic polymers, and crystalline copolymers of propylene with ethylene and/or $C_4$–$C_{10}$ α-olefins, such as, for example, 1-butene, 1-hexene, 4-methyl-1-pentene or 1-octene, in which the total content of comonomer ranges from 0.05% to 20% by weight relative to the weight of the copolymer, or blends of the said copolymers with isotactic or mainly isotactic propylene homopolymers.

Other suitable polyolefins are saturated and unsaturated elastomers, such as ethylene-α-olefin rubbers, that is to say copolymers of ethylene with one or more types of $C_3$–$C_{10}$ α-olefin and, optionally, a diene. Examples of α-olefins include propylene, 1-butene, 1-pentene, 1-hexene and 1-octene. The ethylene content is generally up to about 75% by weight. Examples of dienes include 1,4-hexadiene, 1,5-hexadiene, ethylidene-1-norbornene and dicyclopentadiene. The dienes are generally in a content of from 1% to 10% by weight. Other examples of the said rubbers are copolymers of ethylene and vinyl acetate and derivatives thereof, copolymers of ethylene and acrylic acid esters or derivatives thereof, copolymers of ethylene and methacrylic acid or derivatives thereof, or the like. Further examples of unsaturated elastomers are butadiene rubbers, styrene-butadiene rubbers (SBR), norbornadiene rubber (NR), and the like.

Blends of the abovementioned polyolefins are also possible. Examples of such blends are heterophasic copolymers comprising (I) a propylene homopolymer and/or one of the said crystalline propylene copolymers and (II) an elastomeric fraction comprising one or more of the said elastomeric copolymers, typically prepared according to known processes by mixing the components in the melt, or by sequential polymerization, and generally containing the elastomeric fraction (II) in an amount of from 5% to 80% by weight.

The esters of formula (I) as crosslinking agents are generally used in an amount of from 0.01 to 8 parts by weight, preferably from 0.15 to 5 parts by weight and more preferably from 0.15 to 2 parts by weight, per 100 parts of crosslinkable polymer.

The amount of free-radical initiator in the crosslinking process generally ranges from 0.1% to 10% by weight, preferably from 0.2% to 5% by weight and more preferably from 0.2% to 2% by weight, relative to the crosslinkable polymer.

Suitable free-radical initiators have a decomposition half-life of 10–200 seconds in the temperature range in which crosslinking reaction is normally carried out (generally from 100° C. to 240° C. for polyolefins).

Examples of free-radical initiators are organic peroxides, for instance diacyl peroxides, dialkyl peroxides, peroxyesters and perketals. Specific examples thereof are benzoyl peroxide, dicumyle peroxide, di-t-butylperoxydiisopropylbenzene, 2,5-dimethyl-2,5-di(t-butylperoxy)hexane and 1,1-di-t-butylperoxy-3,3,5-trimethylcyclohexane.

An indirect evaluation of the degree of crosslinking may be provided by the amount of gel which is formed by the crosslinking effect, the gel reducing the solubility of the polymer. Such amount is calculated using the following formula:

% of gel=(C—X)×(1/C)×100 in which C is the percentage of the crosslinked polymer in the composition before crosslinking, while X is the soluble fraction of the crosslinked polymer.

This crosslinking process is not specifically limited and may be any conventional process known to those skilled in the art. One example is the dynamic crosslinking process. The crosslinking is normally carried out from 140 to 240° C. for a period of from 1 to 60 minutes. Preferably, the process is carried out under an inert atmosphere, for example nitrogen.

Common additives that are usually used with polymers, in particular polyolefins, for instance heat stabilizers, antioxidants, pigment charges, mineral fillers, flame retardants, antistatic agents and lubricants, may be added to the polymer before, during or after the crosslinking stage.

As stated above, the crosslinked polymers according to the invention show less yellowing than polymers crosslinked with the known furfuryl derivatives, for instance furfuraldazine. A marked decrease in coloration is observed in particular when the esters are used in small amounts, that is to say up to about 0.4 part by weight per 100 parts of the crosslinkable polymer. The following examples are given to illustrate the present invention without, however, constituting a limitation thereof.

The processes used to obtain the property data given in the examples and in the description are described below.

The melting point is measured using a Reichert® Polyvar optical microscope with cross-polarizers, equipped with a Mettler® FP52 programmable heater, and the temperature ramp used is 10° C. per minute.

The volatilization temperature is measured by thermogravimetric analysis carried out using a Mettler® TG50 instrument, and the temperature ramp used is 20° C. per minute.

The xylene-insoluble fraction is determined as follows. A weighed amount of the sample (2 grams) is suspended in 200 mL of anhydrous xylene at room temperature; the suspension is heated to the boiling point of the solvent (135° C.) with continuous stirring, and the solution is maintained at reflux for one hour. The hot solution is then filtered to remove the soluble fraction, and the residue is washed with 50 ml of boiling xylene, until the filtrate no longer shows any precipitation of polymer. The residue is then washed with cold acetone and dried to constant weight.

The melt flow index L (MIL) is measured according to ASTM process D 1238, condition L.

The colour is estimated by eye.

EXAMPLE 1

Synthesis of 1,2-ethanediyl bis[3-(2-furyl)-2-propenoate] (EBFA)

a) Synthesis of 3-(2-furyl)-2-propenoic acid

The following are introduced, in the following order, into a 100 niL three-necked round-bottomed flask equipped with a dropping funnel, a condenser and a mechanical stirrer, under a nitrogen atmosphere: anhydrous pyridine (150 mL), malonic acid (25 g, 0.24 mol) and anhydrous piperidine (0.012 mol). After cooling the solution to 0° C. using an ice bath, furfuraldehyde (23 g) is added. The temperature is then raised to room temperature.

The solution is maintained at the reflux point of the solvent for 3 hours. The pyridine is removed by distillation under reduced pressure. The brown solid is dissolved in ethyl ether. The pyridine and piperidine residues are then extracted with three times 50 mL of 1% HCI solution. After evaporation of the ethyl ether, the reaction product is purified by precipitation with HCI from an aqueous alkaline solution.

The yield of 3-(2-furyl)-2-propenoic acid is 29.01 g (87% by weight).

b) Synthesis of 1,2-ethanediyl bis[3-(2-furyl)-2-propenoate]

$CH_2Cl_2$ (150 mL), 20 g of 2-furylpropenoic acid (0.145 mol), 4.334 g of 1,2-ethanediol (0.07 mol) and 0.4 g of dimethylaminopyridine (0.035 mol) are placed in the same device as that described in a). 30.1 g of dicyclohexylcarbodiimide dissolved in 50 mL of $CH_2Cl_2$ are then added at room temperature.

The mixture is stirred continuously for 90 hours. The precipitated white solid (dicyclohexylurea) thus produced is separated out by filtration through diatomaceous earth (Celite®) and washed on the filter with two portions of $CH_2Cl_2$. Next, the filtered solution is washed first with three times 100 mL of 1% HCI solution, then with two portions of saturated aqueous $K_2CO_3$ solution and finally with distilled water.

Most of the solvent of the solution thus washed is removed by distillation under reduced pressure. The concentrated solution is then left in a refrigerator for 24 hours. The further precipitate (dicyclohexylurea) thus obtained is separated out by filtration as described above. Once all the solvent has been evaporated off, the residue is dissolved in hot heptane and then left to crystallize. The reaction yield is 11.2 g (75%).

The reaction product is a white solid with a melting point of 75° C. and a volatilization temperature of 200° C. (compared with 100° C. for furfuraldazine).

Examples 1–4 and

Comparative Examples 1c–4c

A crystalline propylene homopolymer (MIL of 1 g/10 minutes and xylene-soluble fraction at ambient temperature of 5% by weight) (sold as Moplen® Q30P) is introduced into a Brabender Plastograph™ PL2100 internal mixer. The temperature is raised to 180° C. After 4 minutes at the said temperature, the crosslinking agent is added to the polymer; the components are mixed at 180° C. and at a speed of 80 rpm. 2 minutes after adding the crosslinking agent, (2,5-dimethyl-2,5-di-tert-butylperoxy)hexane is added in an amount of 0.8 part by weight per 100 parts by weight of polymer, with continued mixing. The total mixing time is 15 minutes.

Reference Example 1r

Example 1 is repeated, except that the crosslinking agent is not added. The polymer thus treated has an MIL of 171 g/10 minutes.

Table 1 shows the amount of EBFA and furfuraldazine as crosslinking agent used in each example.

Table 2 shows the MIL and xylene-insoluble values for the crosslinked polymers of Examples 1–4 compared with the Comparative Examples 1c–4c. The degree of crosslinking is given by the value of the xylene-insoluble fraction. The xylene-insoluble amounts show that the crosslinking efficiency of EBFA is greater than that of furfuraldazine, for equivalent molar amounts of EBFA and furfuraldazine.

TABLE 1

| Examples and comparative example | EBFA × 10⁻³ mol | EBFA Parts by weight[1] | Furfuraldazine × 10⁻³ mol | Furfuraldazine Parts by weight[1] |
|---|---|---|---|---|
| 1 | 1.06 | 0.32 | — | — |
| 2 | 2.12 | 0.64 | — | — |
| 3 | 3.20 | 0.96 | — | — |
| 4 | 4.24 | 1.28 | — | — |
| 1c | — | — | 2.12 | 0.4 |
| 2c | — | — | 3.20 | 0.6 |
| 3c | — | — | 4.25 | 0.8 |
| 4c | — | — | 5.32 | 1.0 |

[1]Parts per 100 parts by weight of polymer

TABLE 2

Properties of the polymer crosslinked with EBFA

| Examples | MIL (g/10 minutes) | Xylene-insoluble (% by weight) | Colour[1] |
|---|---|---|---|
| 1 | 139 | 0.52 | Pale yellow |
| 2 | 58 | 4.05 | Pale yellow |
| 3 | 22 | 31.9 | Yellow |
| 4 | 14.5 | 37.16 | Yellow |

[1]Assessed by eye

TABLE 3

Properties of the polymer crosslinked with furfuraldazine

| Comparative Examples | MIL (g/10 minutes) | Xylene-insoluble (% by weight) | Colour[1] |
|---|---|---|---|
| 1c | 28.8 | Traces | Dark yellow |
| 2c | 13.8 | 0.71 | Dark yellow |
| 3c | 6.96 | 2.0 | Brown |
| 4c | 6.15 | 16.6 | Brown |

[1]Assessed by eye

Other features, advantages and embodiments of the invention disclosed herein will be readily apparent to those exercising ordinary skill after reading the foregoing disclosures. In this regard, while specific embodiments of the invention have been described in considerable detail, variations and modifications of these embodiments can be effected without departing from the spirit and scope of the invention as described and claimed.

What is claimed is:

1. Diol esters of 3-(2-furyl)-2-propenoic acid having the following general formula:

$$A_2X \qquad (I)$$

in which

A is

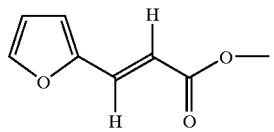

and X is a $C_1$–$C_6$ alkylene group.

2. Esters according to claim 1, in which the alkylene group contains one or more substituents chosen from linear or branched $C_1$–$C_{20}$ alkyl radicals, $C_3$–$C_{18}$ cycloalkyl radicals, $C_6$–$C_{18}$ aryl radicals or $C_7$–$C_{20}$ arylalkyl radicals.

3. Esters according to claim 1, in which the alkylene group contains two, three or four carbon atoms.

4. Esters according to claim 1, chosen from:

methanediyl bis[3-(2-furyl)-2-propenoate];
phenylmethanediyl bis[3-(2-furyl)-2-propenoate];
1,2-ethanediyl bis[3-(2-furyl)-2-propenoate];
1,3-propanediyl bis[3-(2-furyl)-2-propenoate]:
1,2-propanediyl bis[3-(2-furyl)-2-propenoate];
1,3-butanediyl bis[3-(2-furyl)-2-propenoate];
1,4-butanediyl bis[3-(2-furyl)-2-propenoate];
2,3-butanediyl bis[3-(2-furyl)-2-propenoate];
1,5-pentanediyl bis[3-(2-furyl)-2-propenoate];
1,6-hexanediyl bis[3-(2-furyl)-2-propenoate];
4-methyl-2,4-pentanediyl bis[3-(2-furyl)-2-propenoate].

5. Process for synthesizing the esters according to claim 1, by reacting the corresponding saturated aliphatic alcohols containing two hydroxyl groups (diols) with 3-(2-furyl)-2-propenoic acid or derivatives thereof.

6. Process for synthesizing methanediyl bis[3-(2-furyl)-2-propenoate] by reacting 3-(2-furyl)-2-propenoic acid or the corresponding anhydride with formaldehyde in the presence of an acid catalyst.

7. Process for synthesizing phenylmethanediyl bis[3-(2-furyl)-2-propenoate] by reacting 3-(2-furyl)-2-propenoic anhydride with toluene in the presence of $CrO_3$.

8. Process for crosslinking polymers in the presence of a free-radical initiator and an ester according to claim 1.

9. Process according to claim 8, in which the amount of ester ranges from 0.01 to 8 parts by weight per 100 parts of the crosslinkable polymer.

10. Process according to claim 8, in which the polymer is a polyolefin.

11. Crosslinked polymer obtained by the process of claim 8.

* * * * *